United States Patent
Georgopoulos et al.

(10) Patent No.: US 12,380,968 B2
(45) Date of Patent: Aug. 5, 2025

(54) MULTIPLE CHEMICAL PROGRAMS FOR AN ARRAY OF CHEMICAL REACTORS WITH A SINGLE ARRAY OF REACTANTS

(71) Applicant: INTERNATIONAL BUSINESS MACHINES CORPORATION, Armonk, NY (US)

(72) Inventors: Leonidas Georgopoulos, Zurich (CH); Aleksandros Sobczyk, Ruschlikon (CH); Alain Claude Vaucher, Zurich (CH); Philippe Schwaller, Duedingen (CH); Joppe Geluykens, Zurich (CH); Teodoro Laino, Rueschlikon (CH)

(73) Assignee: International Business Machines Corporation, Armonk, NY (US)

( * ) Notice: Subject to any disclaimer, the term of this patent is extended or adjusted under 35 U.S.C. 154(b) by 1075 days.

(21) Appl. No.: 16/995,862

(22) Filed: Aug. 18, 2020

(65) Prior Publication Data
US 2022/0059193 A1     Feb. 24, 2022

(51) Int. Cl.
G16C 20/10     (2019.01)
B01J 19/00     (2006.01)
G05B 19/4099   (2006.01)

(52) U.S. Cl.
CPC .......... *G16C 20/10* (2019.02); *B01J 19/0033* (2013.01); *B01J 19/0046* (2013.01);
(Continued)

(58) Field of Classification Search
CPC .................. G16C 20/10; B01J 19/0046; B01J 2219/00038; B01J 2219/00585; B01J 2219/00997
See application file for complete search history.

(56) References Cited

U.S. PATENT DOCUMENTS

| 8,934,994 B1 | 1/2015 | Lee |
| 10,332,619 B2 | 6/2019 | Giri |

(Continued)

FOREIGN PATENT DOCUMENTS

| CN | 110534164 A | 12/2019 |
| CN | 111524557 A | 8/2020 |

(Continued)

OTHER PUBLICATIONS

Mell et al., "The NIST Definition of Cloud Computing", Recommendations of the National Institute of Standards and Technology, Special Publication 800-145, Sep. 2011, 7 pages.

(Continued)

*Primary Examiner* — Paul S Hyun
(74) *Attorney, Agent, or Firm* — L. Jeffrey Kelly (57) ABSTRACT

A method for executing multiple chemical programs in parallel in an array of chemical reactors using a single array of substance containers may be provided. The method includes receiving a plurality of chemical programs, building a plurality of records comprising each a chemical program. Thereby, each record includes a key and a data field, wherein the key is indicative of the reactants required for the respective chemical reaction, and wherein the data field includes the chemical program. The method further includes creating an ordered data structure of the data records based on the keys, selecting a next record from the ordered data structure, assigning the selected next record to selected ones of the array of chemical reactors, repeating the steps of selecting and assigning until, as a maximum, each chemical reactor has a defined record assigned to it, and executing the chemical programs according to their defined records in parallel.

19 Claims, 7 Drawing Sheets

(52) U.S. Cl.
CPC ............... *B01J 2219/00038* (2013.01); *B01J 2219/00229* (2013.01); *B01J 2219/00585* (2013.01); *B01J 2219/00695* (2013.01); *G05B 19/4099* (2013.01)

(56) References Cited

U.S. PATENT DOCUMENTS

| | | | |
|---|---|---|---|
| 10,589,248 | B1 | 3/2020 | Doris |
| 11,132,621 | B2 | 9/2021 | Botea |
| 2002/0049548 | A1 | 4/2002 | Bunin |
| 2002/0111782 | A1 | 8/2002 | Klaffke |
| 2003/0223909 | A1* | 12/2003 | Oberbeck ........... B01F 33/3039 422/131 |
| 2004/0003000 | A1 | 1/2004 | Smith |
| 2005/0246316 | A1 | 11/2005 | Lawson |
| 2009/0024575 | A1 | 1/2009 | Wagner |
| 2009/0228445 | A1 | 9/2009 | Gangal |
| 2011/0066632 | A1 | 3/2011 | Robson et al. |
| 2011/0213499 | A1* | 9/2011 | Sturmer ................ F04B 49/065 700/266 |
| 2013/0041683 | A1 | 2/2013 | Boissel |
| 2014/0342358 | A1* | 11/2014 | Dockrill ........... G01N 35/00029 435/7.1 |
| 2016/0103979 | A1 | 4/2016 | Giri |
| 2018/0046930 | A1 | 2/2018 | Kossarian |
| 2018/0093245 | A1 | 4/2018 | Colgan |
| 2019/0147370 | A1 | 5/2019 | Botea |
| 2019/0233751 | A1 | 8/2019 | Medoff |
| 2019/0286791 | A1 | 9/2019 | Takeda et al. |
| 2020/0050947 | A1 | 2/2020 | Kishimoto |
| 2020/0066552 | A1 | 2/2020 | Susa |
| 2020/0168302 | A1 | 5/2020 | Isayev |
| 2022/0058337 | A1 | 2/2022 | Georgopoulos |
| 2022/0059192 | A1 | 2/2022 | Georgopoulos |

FOREIGN PATENT DOCUMENTS

| | | |
|---|---|---|
| CN | 116075899 A | 5/2023 |
| JP | 2023-537933 A | 9/2023 |
| WO | 2019086325 A1 | 5/2019 |
| WO | 2019137954 A1 | 7/2019 |
| WO | 2019179887 A1 | 9/2019 |
| WO | 2020/023650 A1 | 1/2020 |
| WO | 2022037985 A1 | 2/2022 |

OTHER PUBLICATIONS

IBM, List of IBM Patents or Patent Applications Treated as Related, Appendix P, dated Sep. 4, 2020, 2 pages.

Pending U.S. Appl. No. 16/995,853, filed Aug. 18, 2020, entitled "Generating Organic Synthesis Procedures From Simplified Molecular-Input Line-Entry System Reaction", 44 pages.

Pending U.S. Appl. No. 16/995,858, filed Aug. 18, 2020, entitled "Running Multiple Experiments Simultaneously on an Array of Chemical Reactors", 38 pages.

Coley et al., "A robotic platform for flow synthesis of organic compounds informed by AI planning", Research Article Summary, Science 365, Aug. 9, 2019, pp. 1-11.

Mysore et al., "Automatically Extracting Action Graphs from Materials Science Synthesis Procedures", Nov. 28, 2017, Workshop on Machine Learning for Molecules and Materials at NIPS 2017, Long Beach, CA, USA, 11 pages.

Nicolaou et al., "Context Aware Data-Driven- Retrosynthetic Analysis", Journal of Chemical Information and Modeling, Published Apr. 13, 2020, pp. 2728-2738.

Notification of Transmittal of the International Search Report and the Written Opinion of the International Searching Authority, or the Declaration, File Reference P202000807, International application No. PCT/EP2021/072165, Mailed on Nov. 17, 2021, 16 pages.

Vaucher et al., "Automated extraction of chemical synthesis actions from experimental procedures", nature communications, Article, 2020, pp. 1-11.

Vaucher et al., "Inferring experimental procedures from text-based representations of chemical reactions", nature communications, Article, 2021, pp. 1-11.

Almeida et al., Synthetic organic chemistry driven by artificial intelligence, Nature Reviews | Chemistry, vol. 3 | Oct. 2019, pp. 589-604.

Coley et al., "Autonomous Discovery in the Chemical Sciences Part I: Progress", Machine Learning, Chem. Int. Ed. 2020, 59 pp. 22858-22893.

Kochev et al., "Ambit-SMIRKS: a software module for reaction representation, reaction search and structure transformation", Journal of Chemonformatics, 2018 10:42, 29 pages.

Lin et al., "BigSMILES: A Structurally-Based Line Notation for Describing Macromolecules", Research Article, ACS Cent. Sci, 2019, 5, pp. 1523-1531.

Nair et al., "Data-driven Chemical Reaction Prediction and Retrosynthesis", Artificial Intelligence in Swiss Chemical Research, 2019, 73, No. 12, pp. 997-1000.

Sandfort et al., "a Structure-Based Platform for Predicting Chemical Reactivity", Chem, CellPress, Article, Chem 6, Jun. 11, 2020, 104 pages.

Japan Patent Office, "Notice of Reasons for Refusal," Oct. 15, 2024, 6 Pages, JP Application No. 2023-509391.

Liu et al. "Retrosynthetic Reaction Prediction Using Neural Sequence-to-Sequence Models", ACS Central Science, Sep. 5, 2017, vol. 3, Issue 10, pp. 1103-1113.

The State Intellectual Property Office of People's Republic of China, "First Office Action", May 30, 2025, 37 Pages, CN Application No. 202180056099.5.

* cited by examiner

MULTIPLE CHEMICAL PROGRAMS FOR AN ARRAY OF CHEMICAL REACTORS WITH A SINGLE ARRAY OF REACTANTS

BACKGROUND

The invention relates generally to a method for multiple chemical programs, and more specifically, to a method for executing multiple chemical programs in parallel in an array of chemical reactors using a single array of substance containers. The invention relates further to a related control system for controlling an execution of multiple chemical programs in parallel in an array of chemical reactors using a single array of substance containers, and a computer program product.

SUMMARY

According to one aspect of the present invention, a method for executing multiple chemical programs in parallel in an array of chemical reactors using a single array of substance containers may be provided. The method may include receiving a plurality of chemical programs indicative of chemical reactions using reactants from the array of substance container and building a plurality of records, wherein each record relates to one of the plurality of chemical programs. Thereby each record may include a key and a data field. The key may be a string of sorted characters indicative of the reactants required for the respective chemical reaction, and the data field may include the chemical program.

The method may further include creating an ordered data structure of the data records based on the keys, selecting a next record from the ordered data structure, assigning the selected next record to selected ones of the array of chemical reactors, repeating the steps of selecting and assigning until, as a maximum, each chemical reactor has a defined record assigned to it, and executing the chemical programs according to their defined records in parallel.

According to another aspect of the present invention, a control system for controlling an execution of multiple chemical programs in parallel in an array of chemical reactors using a single array of substance containers may be provided. The control system may include receiving a plurality of chemical programs indicative of chemical reactions using reactants from the array of substance container and building means adapted for building a plurality of records. Each record may relate to one of the plurality of chemical programs. Each record may include a key and a data field; the key is a string of sorted characters indicative of the reactants required for the respective chemical reaction; and the data field may include the chemical program.

The control system may further include creation means adapted for creating an ordered data structure of the data records based on the keys, selection means adapted for selecting a next record from the ordered data structure, assignment means adapted for assigning the selected next record to selected ones of the array of chemical reactors, repetition means adapted for repeating, in particular controlling the repetition, the steps of selecting and assigning until, as a maximum, each chemical reactor has a defined record assigned to it, and controlling means adapted for controlling an execution of the chemical programs according to their defined records in parallel.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain means for storing, communicating, propagating or transporting the program for use, by, or in connection, with the instruction execution system, apparatus, or device.

BRIEF DESCRIPTION OF THE DRAWINGS

It should be noted that embodiments of the invention are described with reference to different subject-matters. In particular, some embodiments are described with reference to method type claims, whereas other embodiments are described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above, and further aspects of the present invention, are apparent from the examples of embodiments to be described hereinafter and are explained with reference to the examples of embodiments, but to which the invention is not limited.

Preferred embodiments of the invention will be described, by way of example only, and with reference to the following drawings.

DETAILED DESCRIPTION

Performing chemical experiments for a synthesis of new molecules in the chemical, biochemical or pharmaceutical area is time-consuming as well as labor- and cost intensive. In order to at least partially automate such synthesis experiments, chemical robots have been introduced allowing a software based experiment designed in which a limited number of ingredients for the experiments may react, e.g., in a reaction chamber to produce a designed experiment output instead of conducting such wet-lab experiments by humans. Such chemical robots typically source the reactants from an array of potential reactants in which the reactants are stored. Time is a major constraint in conducting a large multitude of chemical experiments. However, due to the many required manual tasks to control such semi-automated experiment environments, it cannot be guaranteed that the equipment makes best use of the time available.

In the process of developing new pharmaceuticals, chemical experiments may be required in which a large number of similar reactions or reaction types may be conducted. Thereby, only variants of a target substance may be produced. This may also be the case for intermediate products along an experiment path, i.e., intermediate products that may be required to be produced from typically comparably simple starting reactants to a complex end product. The intermediate products may also be unstable and may have different half-times. Additionally, it may happen that identical intermediate products may be produced during a plurality of different experiments that are otherwise completely independent from each other.

The proposed concept may take this situation as a starting point to increase the efficiency with which multiple experiments may be conducted.

In the context of this description, the following conventions, terms and/or expressions may be used:

The term 'chemical program' may denote a recipe for or a procedure of building a chemical compound, i.e., end product of a chemical reaction, describing a step-by-step approach how to treat the reactants, intermediate products and related experimental conditions, like temperature, stirring phases, humidity, present catalysts, etc.

The term 'chemical reactors' may denote a plurality of different or identical chemical reactors connectable to an array of containers comprising reactants for a plurality of chemical experiments. In general, a chemical reactor may be an enclosed volume in which a chemical reaction may take place. A chemical reactor may also be part of a chemical robot. A chemical robot may include a plurality of chemical reactors and containers comprising reactants, containers to store intermediate products, and/or the end product.

The term 'substance container' may denote a reservoir, vessel or tank adapted for storing the reactants required for the chemical experiments. The substance container may be selectable and can be connected to the chemical reactors according to the chemical programs.

The term 'record' may denote a data structure comprising a key field and a data field. The key field may hold a string of symbols for the reactants required for the chemical experiment which "recipe" may be described in a standardized form as a string in the data field of the record.

The term 'key' may denote a field of a record by which the record may be selected.

The term 'data field' may denote a string field of the record comprising the chemical program.

The term 'ordered data structure' may denote a sequence of records sorted by the key field.

The term 'hash value' may denote any function value that may be used to map data of arbitrary size to fixed-size values. The values returned by a hash function are called hash values, hash codes, digests, or simply hashes. The values are used to index a fixed-size table denoted as a hash table.

The term 'character', in particular a character of the string for representing chemical substances or reactants, may denote and represent a symbol or letter or any other abstract bit combination and may not only be limited to Latin letters. The characters may be encoded according to a predefined encoding table (e.g., Base32, Base64, or similar).

The proposed method for executing multiple chemical programs in parallel in an array of chemical reactors using a single array of substance containers may offer multiple advantages, contribution and technical effects:

The proposed concept addresses major shortcomings of existing solutions of marketable chemical reactors conducting chemical experiments at least semi-automated. By building the ordered data structure comprising records with keys comprising symbols for the reactants and data fields comprising the chemical programs, an ordered sequence of conducting the chemical experiments may be defined. Additionally, by using symbols describing the reactants as a sorting mechanism via the keys, a grouping of chemical experiments may happen in a way in which chemical experiments, requiring the same or only slightly different reactants as starting point, may be grouped together.

This may have the advantage that the substance container as well as related connection pipes may not have to be washed, cleaned and refilled again and again with changing reactants. The sorting via the keys in the ordered data structure may define a sequence of chemical experiments reducing the reconfiguration of the array of chemical reactors with its related substance containers significantly. This may save large amounts of time, reconfiguration efforts, waste (from the washing process) as well as initial and, often expensive, reactants.

Also, the involvement of human, manual tasks may be reduced due to the lower number of changes in and with the substance containers. Hence, the number of chemical experiments for developing new compounds or pharmaceuticals may be conducted with higher efficiency. This may reduce error rates (e.g., due to wrongly filled substance containers, incomplete washing processes, etc.) and a higher rate of successful chemical experiments at lower costs and at a higher degree of automation.

According to one practical embodiment of the method, the string may be a concatenation of unique identifiers of required reactants in the substance array for one of the chemical programs. The identifiers of the required reactants may be chemical formulas or a mapping to a completely different lexicographical system that may be used. However, it may be ensured that the reactants may be clearly identified. Additionally, the unique identifiers of the required reactants may be sorted lexicographically in their sequence.

According to another embodiment of the method, the string may be a hash value of unique identifiers of required reactants in the substance array for one of the chemical programs. This may make it possible to further group reactants by using a hash function that may convert given similar chemical formulas into a target value with only a small distance value of a related distance function. One option may be in using a locality sensitive hashing function (LSH).

According to one embodiment of the method, the selection may be performed in a sequence the plurality of chemical programs have been received. Thus a 1:1 relation may exist between a sequence of received chemical programs and the sequences may be executed. However, other sequences may be defined based on predefined rules. For example, short running chemical programs may be executed before longer running experiments may be selected. According to another rule, those experiments may be executed first that optimize the usage of the reactors or the reactants such that no replenishment of the reactant containers may be required, or, at least, significantly reduced.

According to another embodiment of the method, the chemical programs may be received in a batch at once. This batch mode may enable an optimized sequence of execution of the chemical programs because all constraints in terms of dependencies, required reactants, expected execution time, etc., may be known from the beginning.

According to another embodiment of the method, the chemical programs may be received sequentially. This mode of operation may be more suitable for a laboratory use in which the chemical programs may be developed from a plurality of different scientist. They may not work under a joint schedule. Hence, the chemical program may be sent to the control system for the chemical experiments once they are ready. Here, they may be buffered until a predefined number of chemical programs may have been received.

According to one advantageous embodiment of the method, a selected chemical reaction may be executed in multiple containers in parallel and/or wherein multiple containers include the same reactant. Thus, if the capacity of one chemical reactor may not be sufficient to produce the desired chemical end product in large enough amounts, the required chemical reaction may be spread across different reactors. Other optimization options may also be used.

According to embodiments of the method, the chemical reactors may be selected out of the group comprising batch reactors, continuous stirred tank reactors, plug flow reactors, semi-batch reactors, and microfluidic reactors. Hence, generally there are not real restrictions on the type of reactors one they are connectable to reactants container an intermediate or end product containers. Additionally, the reactors may have the option to be controlled externally.

According to an enhanced embodiment of the method, the data structure may be selected out of the group comprising a tree structure, a sorted table, a heap data structure, and an ordered linked list. Hence, a defined sequence shall be derivable from the date structure the records may be included in. Also, other data structures may be used allowing which may imply a sorting order.

According to an advanced embodiment of the method, an alphabet may be used to map the chemical reactants to elements of the alphabet wherein a lexicographical order of the chemical reactants depends on at least one characteristic of the reactants. One of such characteristics may be the stability of the reactants or also the end product of the chemical reaction. Many other lexicographical order systems may be implemented.

According to an efficient embodiment, the method may also include, after one of the parallel executed chemical programs has finished, selecting, assigning and executing a next chemical program, in the chemical reactor in which the execution had been finished. This may address a situation in which the time required to finish a chemical program differs from chemical reactor to chemical reactor. Once a chemical program has been finished on one—or also more than one—chemical reactor, the chemical reactor may be used for a next chemical program even if other chemical programs are still being executed in the rest of the reactors. This way, the efficiency of the parallel execution could be enhanced in the sense of an asynchronous parallel execution.

In the following, a detailed description of the figures will be given. All instructions in the figures are schematic. Firstly, a block diagram of an embodiment of the inventive method for executing multiple chemical programs in parallel in an array of chemical reactors using a single array of substance containers is given. Afterwards, further embodiments, as well as embodiments of the related control system for controlling an execution of multiple chemical programs in parallel will be described.

Figure 1:
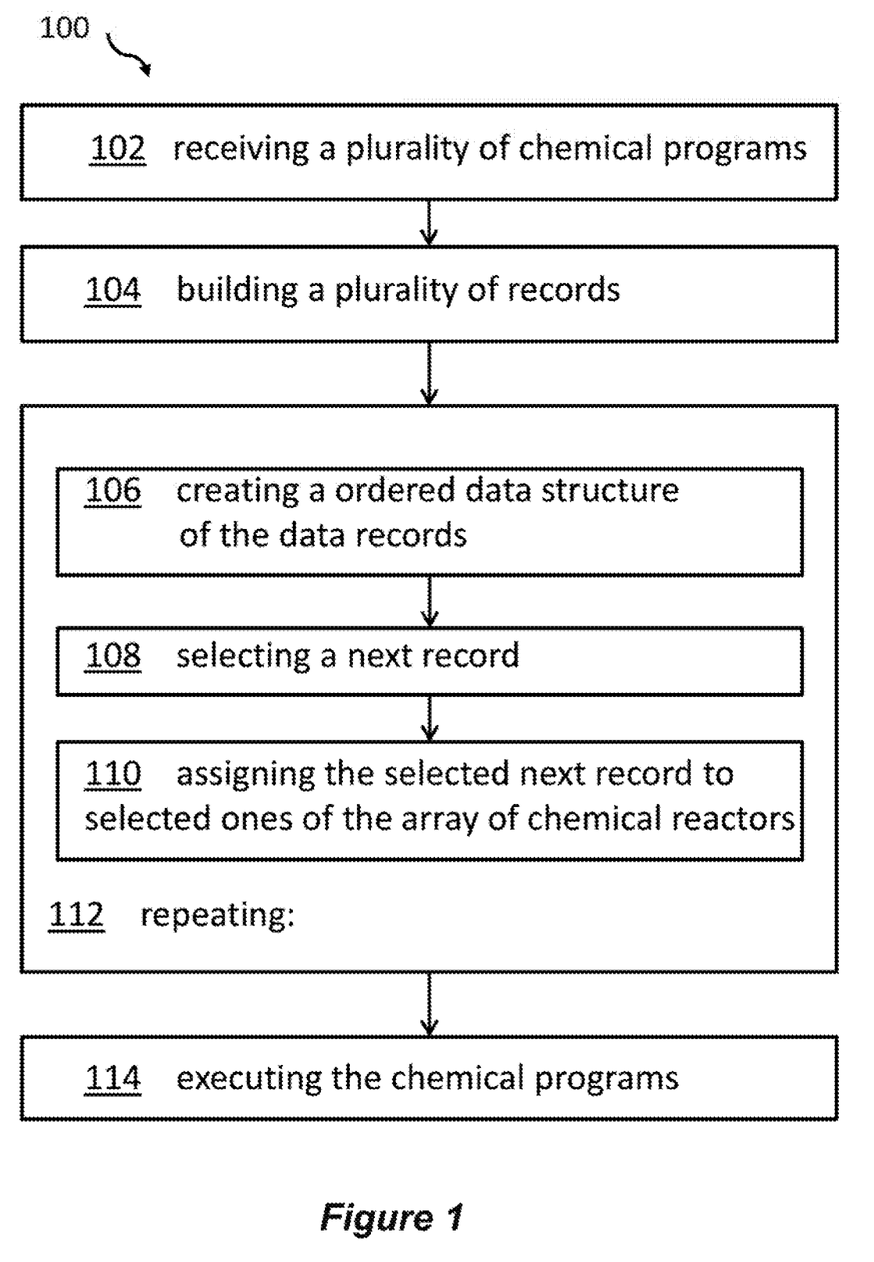
FIG. 1 shows a block diagram of an embodiment of the inventive method for executing multiple chemical programs in parallel in an array of chemical reactors using a single array of substance containers.

FIG. 1 shows a block diagram of a preferred embodiment of the method 100 for executing multiple chemical programs in parallel in an array of chemical reactors using a single array of substance containers. The method 100 includes receiving, 102, a plurality of chemical programs indicative of chemical reactions using reactants from the array of substance containers and building, 104, a plurality of records. Each record relates to one of the plurality of chemical programs and each record includes a key and a data field. Thereby, the key is a string of sorted characters, e.g. lexicographically sorted, and the characters can be letters, numbers, symbols, or a mixture thereof from a defined alphabet. Each of the reactants is an element of this alphabet. The string of sorted characters is indicative of the reactants required for the respective chemical reaction. Additionally, the data field includes the chemical program.

Furthermore, the method 100 includes creating, 106, an ordered data structure of the data records based on the keys, selecting, 108, a next record from the ordered data structure, and assigning, 110, the selected next record to selected ones of the array of chemical reactors.

Moreover, the method 100 includes repeating, 112, the steps of creating, 106, selecting, 108, and assigning, 110. The repeating, 112, continues until, as a maximum, in particular if less records are available than reactors, each chemical reactor has a defined record assigned to it.

The method 100 includes executing, 114, the chemical programs according to their defined records, in parallel.

Figure 2:
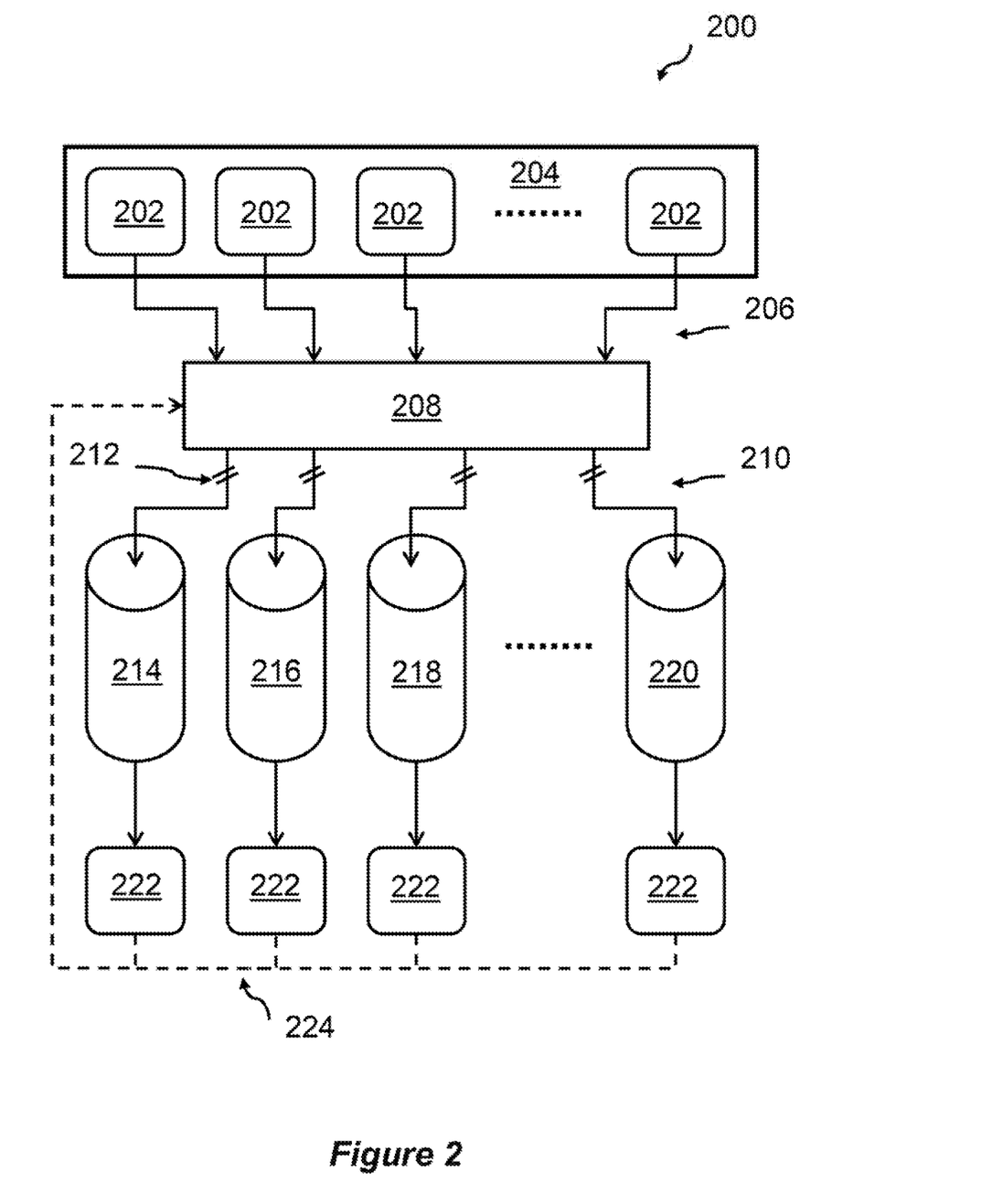
FIG. 2 shows a block diagram of an embodiment of a plurality of reactant containers and chemical reactors.

FIG. 2 shows a block diagram of an embodiment 200 of an array 204 of a plurality of reactants containers 202 together with an array of chemical reactors 214, 216, 218, . . . , 220 instrumental for the proposed concept. The reactant containers 202 are individually connected via pipe layer 206 to a valve and direction unit 208 which is on the other side connected via pipe layer 210 to one or more pipes per chemical reactor 214, 216, 218, . . . , 220. The parallel lines 212 indicate that more than one pipe may exist between the valve and direction unit 208 and the individual chemical reactors 214, 216, 218, . . . , 220. On the output side of the chemical reactors 214, 216, 218, . . . , 220—connected in a 1:1 fashion—a plurality of chemical reaction product containers 222 exist. These product containers 222 may also be used for an intermediate storage, intermediate products from individual ones of the chemical reactors 214, 216, 218, . . . , 220. Additionally, there may be pipe connections 224 between the product containers 222 and the valve and direction unit 208 in order to use intermediate products from the product containers 222 for subsequent reactions in the chemical reactors 214, 216, 218, . . . , 220 to finally produce the chemical (end) product.

Figure 3:
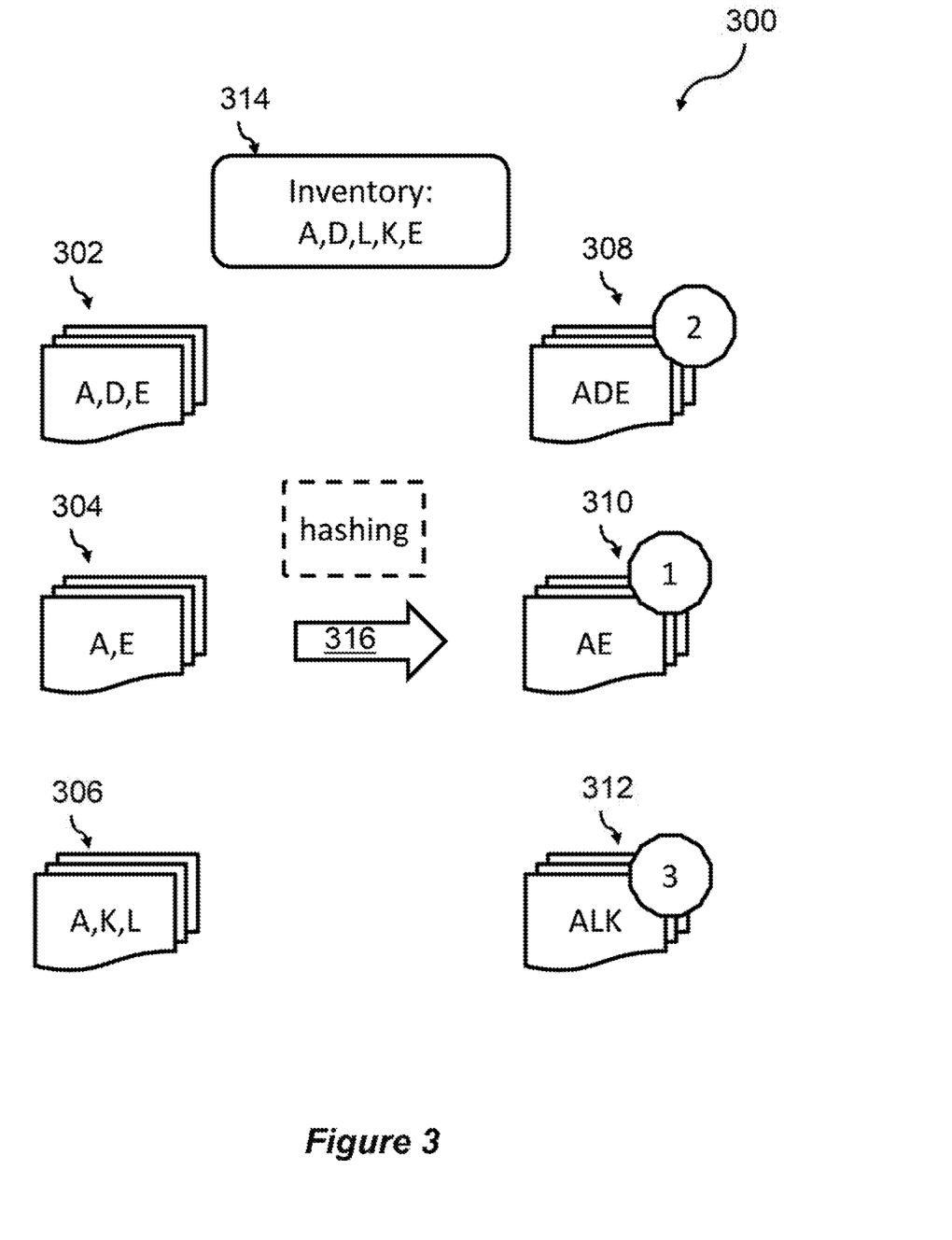
FIG. 3 shows a block diagram of an embodiment of received chemical programs and a reordering of them.

FIG. 3 shows a block diagram 300 of an embodiment of received chemical programs and a reordering of them. The left column of icons shows received chemical programs 302, 304, . . . , 306. Thereby, it should be noted that reference numeral 302 (as well as 304, 306) relates to a plurality (not exactly three as exemplarily shown) of chemical programs. However, each group of the same reference numeral—i.e., 302, 204, . . . , 306—denotes chemical programs (typically different ones) requiring the same reactants. I.e., chemical programs 302 require the reactants E, D, A, wherein the chemical programs 304 require only the two reactants A and E, and so forth.

The received chemical programs 302, 304, . . . , 306 are then converted, 316, to respective records 308, 310, . . . , 312 with a key comprising the reactants in a lexicographically sorted order. Hence, the records 308 relating to the chemical program 302 requiring the reactants E, D, A will have a key value of ADE and so on. The sorting of the reactants symbols will be performed according to the predefined rules of the selected alphabet.

The data field of the record is then the received chemical program. Additionally, a hash function may be used to build the hashed key values of the respective records 308, 310, . . . , 312, starting from the ingredients, i.e., reactants, of the chemical programs.

Due to the lexicographically sorting, also the key of the records are sorted now and can at least be included into a data structure defining the sequence of the chemical experiments to be conducted. Hence, the chemical experiments relating to the chemical programs and, hence, to the records 310 will be applied first, the chemical programs 308 second and the chemical programs 312 last in the here described exemplary set-up.

Additionally, the single array of substance containers 314 (equivalent to 204 of FIG. 2) is shown symbolically.

Figure 4:
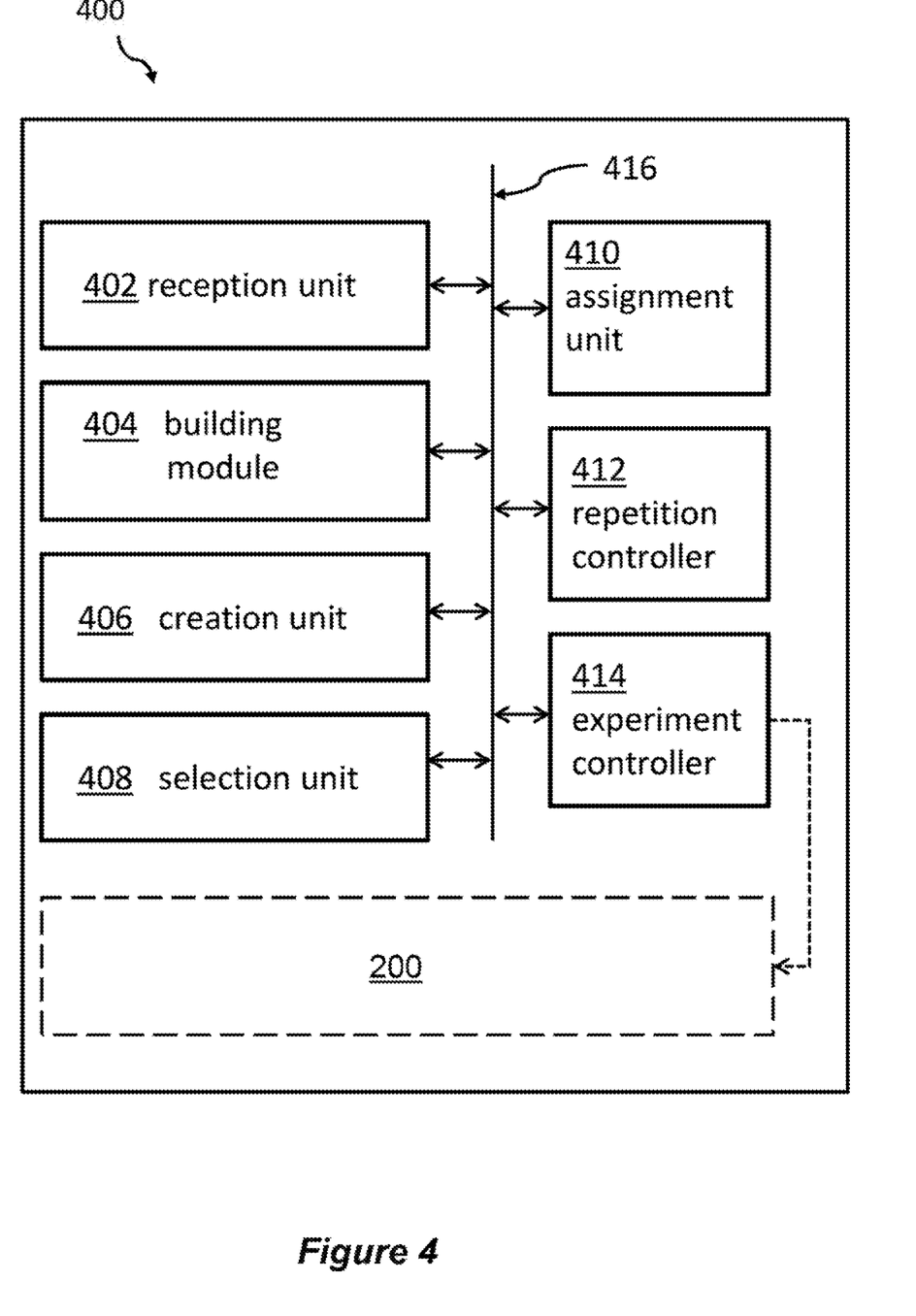
FIG. 4 shows a block diagram of an embodiment of the inventive control system for controlling an execution of multiple chemical programs in parallel.

FIG. 4 shows a block diagram of an embodiment of the inventive control system 400 for controlling an execution of multiple chemical programs in parallel in an array of chemical reactors using a single array of substance containers. The control system 400 includes receiving means, in particular the reception unit 402, adapted for receiving a plurality of chemical programs indicative of chemical reactions using reactants from the array of substance containers. The control system 400 includes building means, in particular the building unit 404, adapted for building a plurality of records. Each record relates to one of the plurality of chemical programs and each record includes a key and a data field. Thereby, the key is a string of sorted characters indicative of the reactants required for the respective chemical reaction and the data field includes the chemical program.

The control system 400 also includes creation means, in particular the creation unit 406, adapted for creating an ordered data structure of the data records based on the keys. The control system 400 includes selection means, in particular the selection unit 408, adapted for selecting a next record from the ordered data structure. The control system 400 includes assignment means, in particular the assignment unit 410, adapted for assigning the selected next record to selected ones of the array of chemical reactors.

The repetition means, in particular the repetition controller 412, are adapted for controlling a repeating of the steps of selecting and assigning until, as a maximum, each chemical reactor has a defined record assigned to it. The controlling means, in the repetition controller 412, is adapted for controlling an execution of the chemical programs according to their defined records in parallel. The experiment controller, 414, is adapted for controlling the array 204 of the plurality of reactants containers 202 together with the array of chemical reactors 214, 216, 218, . . . , 220 as well as the valve and direction unit 208 (see FIG. 2, a block diagram of the embodiment 200).

It may be noted that the reception unit 402, the building unit 404, the creation unit 406, the selection unit 408, the assignment unit 410, and the repetition controller 412 can be electrically connected to each other for a signal and/or data exchange. As an alternative to the 1:1 electrical connections, the mentioned units and modules can be connected via a controller system internal bus system, for example, communications fabric 518 shown in FIG. 5.

Figure 5:
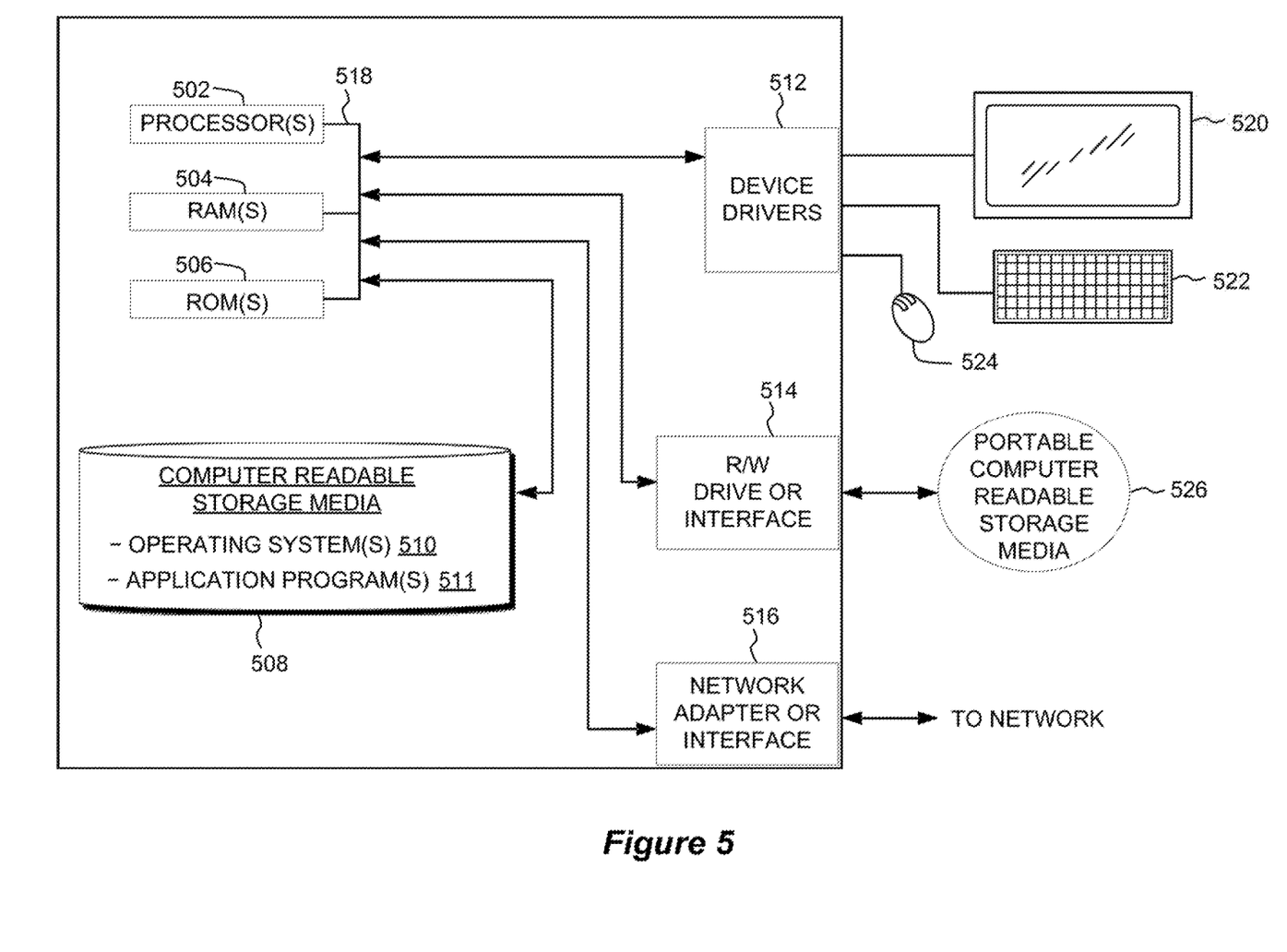
FIG. 5 shows an embodiment of a computing system comprising the control system according to FIG. 4.

Embodiments of the invention may be implemented together with virtually any type of computer, regardless of the platform being suitable for storing and/or executing program code. FIG. 5 shows, as an example, a computing device suitable for executing program code related to the proposed method.

Referring now to FIG. 5, a block diagram of components of a computing device, in accordance with an embodiment of the present invention, is shown. It should be appreciated that FIG. 5 provides only an illustration of an implementation and does not imply any limitations with regard to the environments in which different embodiments may be implemented. Many modifications to the depicted environment may be made.

The computing device may include one or more processors 502, one or more computer-readable RAMs 504, one or more computer-readable ROMs 506, one or more computer readable storage media 508, device drivers 512, read/write drive or interface 514, network adapter or interface 516, all interconnected over a communications fabric 518. Communications fabric 518 may be implemented with any architecture designed for passing data and/or control information between processors (such as microprocessors, communications and network processors, etc.), system memory, peripheral devices, and any other hardware components within a system.

One or more operating systems 510, and one or more application programs 511 are stored on one or more of the computer readable storage media 508 for execution by one or more of the processors 502 via one or more of the respective RAMs 504 (which typically include cache memory). For example, a program for executing multiple chemical programs in parallel in an array of chemical reactors using a single array of substance containers, may be stored on the one or more of the computer readable storage media 508. In the illustrated embodiment, each of the computer readable storage media 508 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

The computing device may also include the R/W drive or interface 514 to read from and write to one or more portable computer readable storage media 526. Application programs 511 on the computing device may be stored on one or more of the portable computer readable storage media 526, read via the respective R/W drive or interface 514 and loaded into the respective computer readable storage media 508.

The computing device may also include the network adapter or interface 516, such as a TCP/IP adapter card or wireless communication adapter (such as a 4G wireless communication adapter using OFDMA technology). Application programs 511 may be downloaded to the computing device from an external computer or external storage device via a network (for example, the Internet, a local area network or other wide area network or wireless network) and network adapter or interface 516. From the network adapter or interface 516, the programs may be loaded onto computer readable storage media 508. The network may comprise copper wires, optical fibers, wireless transmission, routers, firewalls, switches, gateway computers and/or edge servers.

The computing device may also include a display screen 520, a keyboard or keypad 522, and a computer mouse or touchpad 524. Device drivers 512 interface to display screen 520 for imaging, to keyboard or keypad 522, to computer mouse or touchpad 524, and/or to display screen 520 for pressure sensing of alphanumeric character entry and user selections. The device drivers 512, R/W drive or interface 514 and network adapter or interface 516 may comprise hardware and software (stored on computer readable storage media 508 and/or ROM 506).

Additionally, the control system 400 for controlling an execution of multiple chemical programs in parallel in an array of chemical reactors using a single array of substance containers may be attached to the communications fabric 518.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access a normalized search engine or related data available in the cloud. For example, the normalized search engine could execute on a computing system in the cloud and execute normalized searches. In such a case, the normalized search engine could normalize a corpus of information and store an index of the normalizations at a storage location in the cloud. Doing so allows a user to access this information from any computing system attached to a network connected to the cloud (e.g., the Internet).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
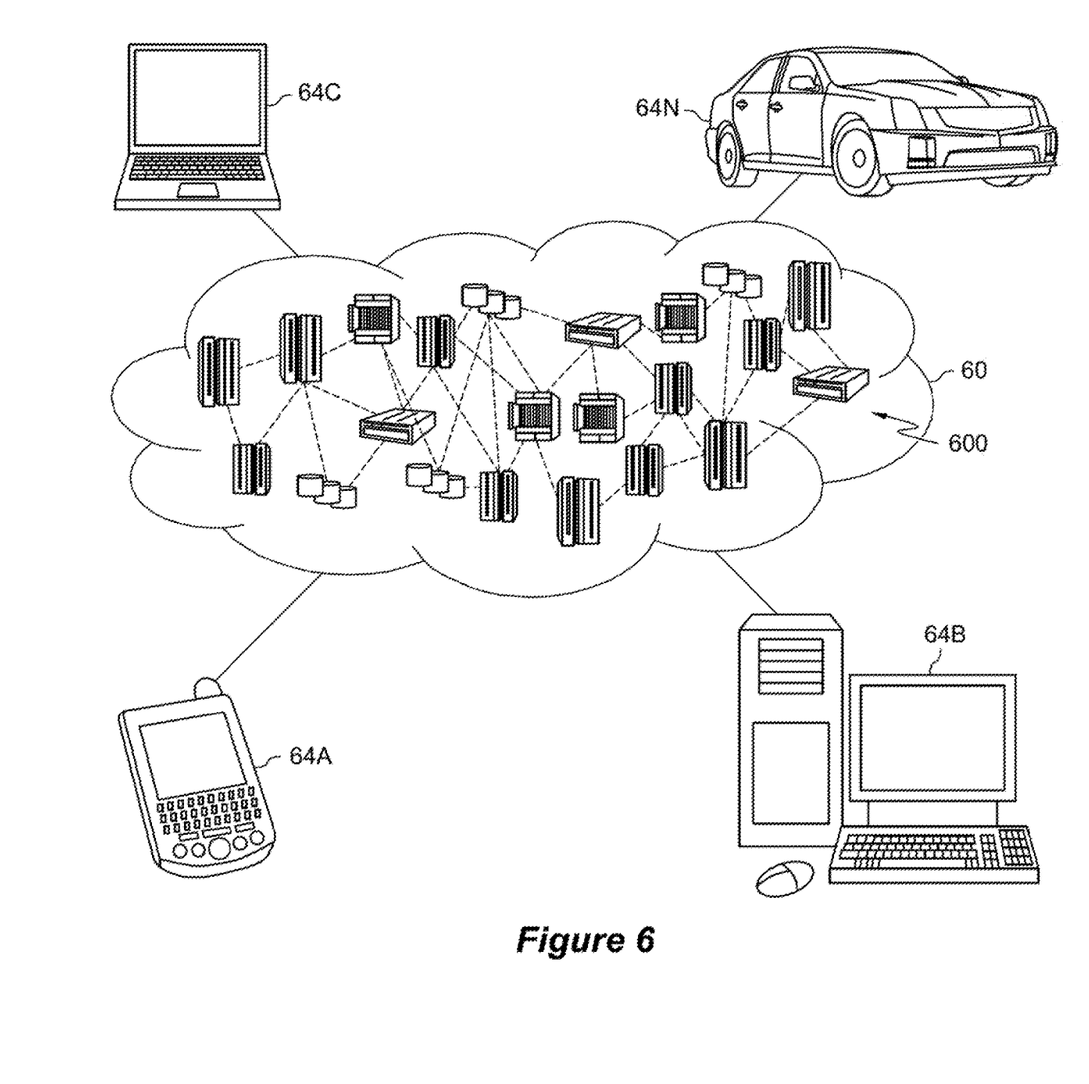
FIG. 6 shows a cloud computing environment according to an embodiment of the present invention.

Referring now to FIG. 6, illustrative cloud computing environment 600 is depicted. As shown, cloud computing environment 600 includes one or more cloud computing nodes 610 with which local computing devices used by cloud consumers, such as, for example, personal digital assistant (PDA) or cellular telephone 640A, desktop computer 640B, laptop computer 640C, and/or automobile computer system 640N may communicate. Cloud computing nodes 610 may communicate with one another. They may be grouped (not shown) physically or virtually, in one or more networks, such as Private, Community, Public, or Hybrid clouds as described hereinabove, or a combination thereof. This allows cloud computing environment 600 to offer infrastructure, platforms and/or software as services for which a cloud consumer does not need to maintain resources on a local computing device. It is understood that the types of computing devices 640A-N shown in FIG. 6 are intended to be illustrative only and that cloud computing nodes 610 and cloud computing environment 600 can communicate with any type of computerized device over any type of network and/or network addressable connection (e.g., using a web browser).

Figure 7:
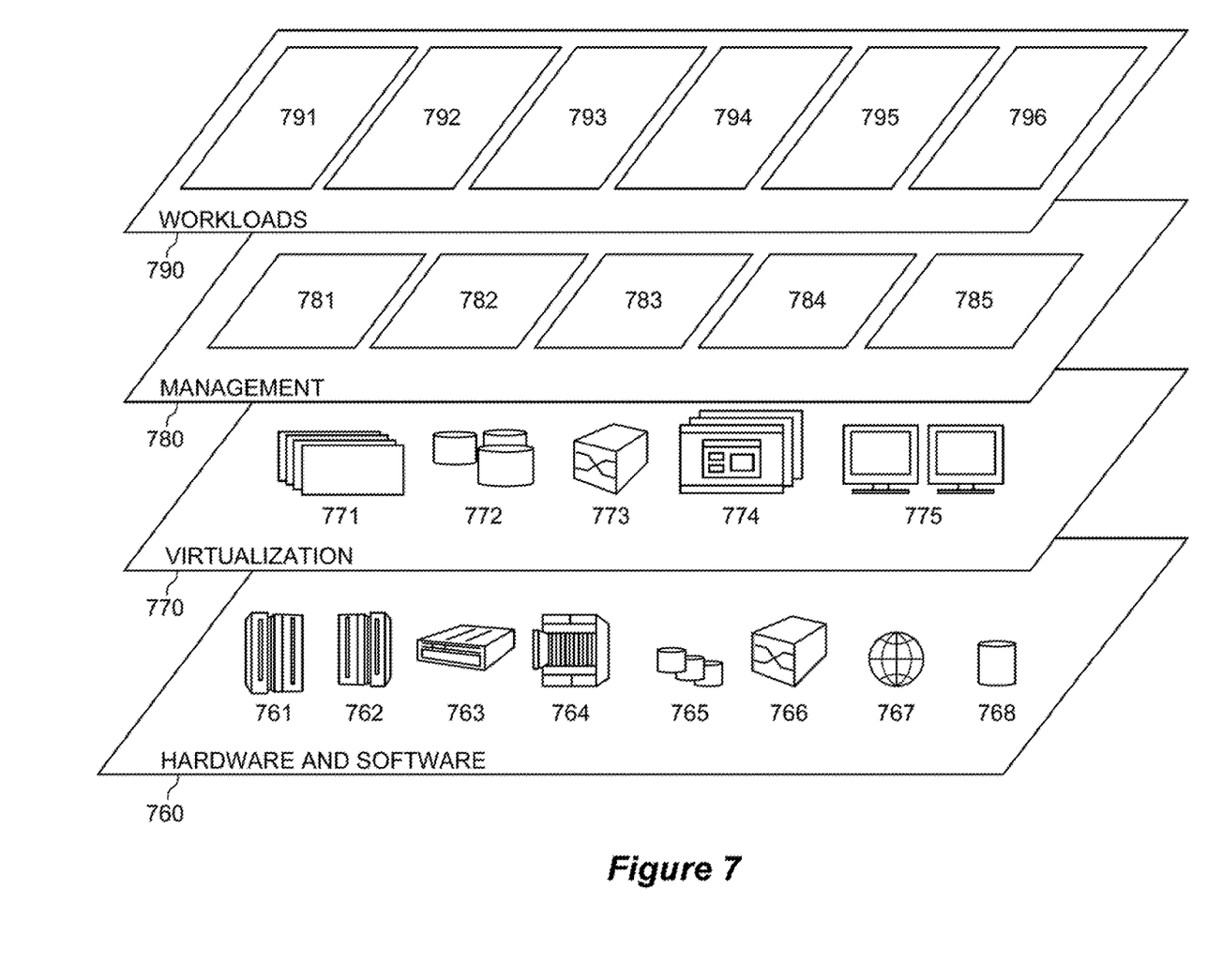
FIG. 7 shows abstraction model layers according to an embodiment of the present invention.

Referring now to FIG. 7, a set of functional abstraction layers provided by cloud computing environment 600 (as shown in FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772, for example the one or more computer readable storage media 508 as shown in FIG. 5; virtual networks 773, including virtual private networks; virtual applications and operating systems 774; and virtual clients 775.

In an example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In an example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 685 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and chemical reaction control management program 796. The chemical reaction control management program 796 may manage 14 execution of multiple chemical programs in parallel in an array of chemical reactors using a single array of substance containers.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for executing a plurality of chemical experiments for synthesis of a new molecule in parallel in an array of chemical reactors using a single array of substance containers, the method comprising:
   receiving information which defines chemical reactions and associated reactants from the single array of substance containers for each of the plurality of chemical experiments for synthesis of the new molecule;
   building a record for each of the plurality of chemical experiments based on the received information, wherein each record comprises a key and a data field, wherein the key is a string of sorted characters indicative of reactants required for respective chemical reactions, and wherein the data field comprises a recipe for synthesizing the new molecule;
   sorting the records into a set of groups, wherein the records in each group of the set of groups are ordered in a sequence, wherein each subsequent record in the sequence comprises a combination of reactants of an immediately preceding record and at least one additional reactant to minimize washing, cleaning and refilling the array of chemical reactors between each chemical reaction;
   assigning each group of the set of groups to at least one chemical reactor of the array of chemical reactors; and
   executing each chemical experiment of the plurality of chemical experiments for synthesis of the new molecule based on the sorted records, wherein each chemical experiment is sequentially performed according to the sequence of each group in the assigned chemical reactor.

2. The method according to claim 1, wherein the string of sorted characters is a concatenation of unique identifiers of required reactants in the single array of substance containers.

3. The method according to claim 1, wherein the string of sorted characters is a hash value of unique identifiers of required reactants in the single array of substance containers.

4. The method according to claim 1, wherein the recipe comprises an end product of the chemical reaction, a step-by-step approach how to treat the reactants, intermediate products, temperature, stirring phases, humidity, and present catalysts.

5. The method according to claim 1, wherein the information regarding the plurality of chemical experiments for synthesis of the new molecule is received in a batch at once.

6. The method according to claim 1, wherein the information regarding the plurality of chemical experiments for synthesis of the new molecule is received sequentially.

7. The method according to claim 1, wherein a chemical experiment of the plurality of chemical experiments is executed in multiple chemical reactors of the array of chemical reactors in parallel and wherein multiple substance containers of the single array of substance containers comprise a same reactant.

8. The method according to claim 1, wherein each chemical reactor of the array of chemical reactors is selected from batch reactors, continuous stirred tank reactors, plug flow reactors and semi-batch reactors.

9. The method according to claim 1, wherein the records for each of the plurality of chemical experiments are ordered in a data structure, wherein the data structure is organized in one of the following: a tree structure, a sorted table, a heap data structure, and an ordered linked list.

10. The method according to claim 1, further comprising:
using an alphabet to map the associated reactants from the single array of substance containers to elements of the alphabet wherein the lexicographical order of the reactants depends on at least one characteristic of the reactants.

11. A computer system for executing a plurality of chemical experiments for synthesis of a new molecule in parallel in an array of chemical reactors using a single array of substance containers, the computer system comprising:
one or more computer processors, one or more computer-readable storage media, and program instructions stored on the one or more computer-readable storage media for execution by at least one of the one or more processors, wherein the computer system is configured such that, when being executed by the at least one of the one or more processors, the program instructions cause the computer system to perform a method comprising:
receiving information which defines chemical reactions and associated reactants from the single array of substance containers for each of the plurality of chemical experiments for synthesis of the new molecule;
building a record for each of the plurality of chemical experiments based on the received information, wherein each record comprises a key and a data field, wherein the key is a string of sorted characters indicative of reactants required for respective chemical reactions, and wherein the data field comprises a recipe for synthesizing the new molecule;
sorting the records into a set of groups, wherein the records in each group of the set of groups are ordered in a sequence, wherein each subsequent record in the sequence comprises a combination of reactants of an immediately preceding record and at least one additional reactant to minimize washing, cleaning and refilling the array of chemical reactors between each chemical reaction;
assigning each group of the set of groups to at least one chemical reactor of the array of chemical reactors; and
executing each chemical experiment of the plurality of chemical experiments for synthesis of the new molecule based on the sorted records, wherein each chemical experiment is performed according to the sequence of each group in the assigned chemical reactor.

12. The computer system according to claim 11, wherein the string of sorted characters is a concatenation of unique identifiers of required reactants in the single array of substance containers.

13. The computer system according to claim 11, wherein the string of sorted characters is a hash value of unique identifiers of required reactants in the single array of substance containers.

14. The computer system according to claim 11, wherein the recipe comprises an end product of the chemical reaction, a step-by-step approach how to treat the reactants, intermediate products, temperature, stirring phases, humidity, and present catalysts.

15. The computer system according to claim 11, wherein the information regarding the plurality of chemical experiments for synthesis of new molecules is received in a batch at once.

16. The computer system according to claim 11, wherein the information regarding the plurality of chemical experiments for synthesis of new molecules is received sequentially.

17. The computer system according to claim 11, wherein a chemical experiment of the plurality of chemical experiments is executed in multiple chemical reactors of the array of chemical reactors in parallel and wherein multiple substance containers of the single array of substance containers comprise a same reactant.

18. The computer system according to claim 11, wherein each chemical reactor of the array of chemical reactors is selected from batch reactors, continuous stirred tank reactors, plug flow reactors and semi-batch reactors.

19. A computer program product for executing a plurality of chemical experiments for synthesis of a new molecule in parallel in an array of chemical reactors using a single array of substance containers, the computer program product comprising:
one or more computer-readable storage medium and program instructions stored on at least one of the one or more computer-readable storage medium, the program instructions executable by a computing system to cause the computing system to perform a method comprising:
receiving information which defines chemical reactions and associated reactants from the single array of substance containers for each of the plurality of chemical experiments for synthesis of the new molecule;
building a record for each of the plurality of chemical experiments based on the received information, wherein each record comprises a key and a data field, wherein the key is a string of sorted characters indicative of reactants required for respective chemical reactions, and wherein the data field comprises a recipe for synthesizing the new molecule;
sorting the records into a set of groups, wherein the records in each group of the set of groups are ordered in a sequence, wherein each subsequent record in the sequence comprises a combination of reactants of an immediately preceding record and at least one additional reactant to minimize washing, cleaning and refilling the array of chemical reactors between each chemical reaction;
assigning each group of the set of groups to at least one chemical reactor of the array of chemical reactors; and
executing each chemical experiment of the plurality of chemical experiments for synthesis of the new molecule based on the sorted records, wherein each chemical experiment is performed according to the sequence of each group in the assigned chemical reactor.

* * * * *